US00PP23363P2

(12) United States Plant Patent
Klemm et al.

(10) Patent No.: US PP23,363 P2
(45) Date of Patent: Jan. 29, 2013

(54) CARNATION PLANT NAMED 'KLEDG10116'

(50) Latin Name: *Dianthus caryophyllus*
Varietal Denomination: KLEDG10116

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 35 days.

(21) Appl. No.: 13/135,764

(22) Filed: Jul. 14, 2011

(51) Int. Cl.
*A01H 5/00* (2006.01)

(52) U.S. Cl. ..... Plt./274

(58) Field of Classification Search ..... Plt./272, Plt./274
See application file for complete search history.

*Primary Examiner* — Susan McCormick Ewoldt
(74) *Attorney, Agent, or Firm* — Jondle & Associates, P.C.

(57) ABSTRACT

A new variety of carnation named 'KLEDG10116' particularly characterized by its white flowers with pink centers, early flowering, and good branching, is disclosed.

1 Drawing Sheet

Genus and species: *Dianthus caryophyllus*.
Variety denomination: 'KLEDG10116'.

BACKGROUND OF THE NEW PLANT

The present invention comprises a new and distinct variety of carnation, botanically known as *Dianthus caryophyllus*, and hereinafter referred to by the variety name 'KLEDG10116'. The new variety is the result of a cross conducted in June 2006 in Stuttgart, Germany between the proprietary female parent carnation plant, '*Dianthus×allwoodii*' (unpatented) and the proprietary male parent, 'Singh' (unpatented). A single plant selection was subsequently chosen for further evaluation and for asexual propagation. The new variety was first propagated via vegetative cuttings in June 2007 in Stuttgart, Germany and has been asexually reproduced repeatedly by vegetative cuttings in Stuttgart, Germany for approximately six to seven generations. 'KLEDG10116' has been found to retain its distinctive characteristics through successive asexual propagations via vegetative cuttings.

'KLEDG10116' has not been made publicly available or sold more than one year prior to the filing date of this application.

SUMMARY OF THE INVENTION

The following are the most outstanding and distinguishing characteristics of this new variety when grown under normal horticultural practices in a greenhouse in Stuttgart, Germany.

1. White flowers with pink centers;
2. Early flowering; and
3. Good branching

DESCRIPTION OF THE PHOTOGRAPH

This new carnation plant is illustrated by the accompanying photograph which shows the flowers and foliage of the plant. The colors shown are as true as can be reasonably obtained by conventional photographic procedures. The photograph was taken in April 2010 of a 5-month-old plant grown from rooted cuttings in a 10 centimeter pot in a glass-covered greenhouse in Stuttgart, Germany under conditions which approximate those generally used in horticultural practice.

DESCRIPTION OF THE NEW VARIETY

The following detailed descriptions set forth the distinctive characteristics of 'KLEDG10116'. The data which define these characteristics were collected from asexual reproductions carried out in Stuttgart, Germany. The plant history was taken in Spring 2010 on 5-month-old plants in 10 centimeter pots that were pinched once at week 45 and grown in a glass-covered greenhouse. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family*.—Caryophyllaceae.
- *Genus and species*.—*Dianthus caryophyllus*.
- *Common name*.—Carnation.

Parentage:
- *Female parent*.—The proprietary carnation '*Dianthus×allwoodii*' (unpatented).
- *Male parent*.—The proprietary carnation 'Sinah' (unpatented).

Plant:
- *Form*.—Potted plant.
- *Habit*.—Upright, round.
- *Height (from top of soil)*.—10.0 cm to 12.0 cm.
- *Width (spread)*.—8.0 cm to 10.0 cm.
- *Life cycle*.—Perennial.
- *Flowering habit*.—Continuous.
- *Time to produce a finished flowering plant*.—4 months.
- *Propagation type*.—Vegetative cuttings.
- *Time to initiate roots*.—16 days.
- *Root description*.—Fine; RHS NN155C (White).
- *Temperature tolerances*.—+30° C. to −15° C.

Branches:
- *Strength*.—Weak.
- *Quantity per plant*.—6 to 8.
- *Color*.—RHS 138B.

*Length*.—5.0 cm to 10.0 cm.
*Diameter*.—0.5 cm.
*Internode length*.—0.4 cm to 1.0 cm.
*Texture*.—Smooth.

Leaves:
*Arrangement*.—Opposite.
*Shape*.—Lanceolate.
*Apex*.—Acute.
*Base*.—Obtuse.
*Margin*.—Entire.
*Color*.—Immature leaf: Upper surface: RHS 137C. Lower surface: RHS 138C. Mature leaf: Upper surface: RHS N137A. Lower surface: RHS N138B.
*Length*.—3.0 cm to 5.0 cm.
*Width*.—0.3 cm to 0.5 cm.
*Texture*.—Smooth.
*Venation pattern*.—Pinnate.
*Venation color*.—Upper surface: RHS 138B. Lower surface: RHS 138C.
*Petioles*.—Absent.

Flowers:
*Blooming habit*.—Small sprays.
*Flower type*.—Double.
*Flowering season*.—Early Spring to late Autumn.
*Lastingness of individual flowers on plant*.—10 days.
*Width*.—4.0 cm to 4.5 cm.
*Depth*.—2.0 cm.
*Shape*.—Round.
*Fragrance*.—Present.
*Number of flowers per plant*.—6 to 8.

Flower buds:
*Color*.—RHS 138B.
*Shape*.—Elliptic.
*Length*.—1.5 cm.
*Diameter*.—0.5 cm.

Petals:
*Arrangement*.—Arranged in several whorls.
*Quantity* (*per flower*).—Greater than 20 to 30.
*Shape*.—Spoon-shaped.
*Apex*.—Obtuse.
*Margin*.—Strongly serrated.
*Base*.—Acute.
*Length*.—2.5 cm.
*Width*.—1.6 cm.
*Color*.—When opening: Upper surface: RHS NN155D and N74D (at eye). Lower surface: RHS NN155D. When fully opened: Upper surface: RHS NN155D and RHS 74D (at eye). Lower surface: RHS NN155D.
*Texture* (*both surfaces*).—Smooth.

Sepals:
*Calyx*.—Form: Cylinder vase. Length: 1.8 cm. Width: 0.8 cm to 1.0 cm.
*Arrangement*.—Fused.
*Quantity* (*per flower*).—4.
*Shape*.—Elliptic.
*Apex*.—Acute.
*Base*.—Obtuse.
*Margin*.—Smooth.
*Length*.—0.7 cm.
*Width*.—0.4 cm.
*Color*.—Upper surface: RHS N138B to RHS N138C. Lower surface: RHS 138C to RHS 138D.
*Texture* (*both surfaces*).—Smooth.

Peduncle:
*Length*.—8.0 cm to 12.0 cm.
*Diameter*.—0.2 cm.
*Texture*.—Smooth.
*Color*.—RHS N138B.

Reproductive organs:
*Pistils*.—Quantity: 1. Stigma color: RHS NN155D. Ovary color: RHS 138B.
*Stamens*.—Quantity: Moderate. Filament: Length: 0.5 cm to 1.0 cm. Color: RHS N155C. Anther color: RHS N155D. Pollen: Amount: Moderate.

Fruit and seed set: None observed.

Disease and insect resistance: No particular resistance or susceptibility to common carnation diseases or insect pests has been observed.

COMPARISON WITH PARENTAL VARIETIES

'KLEDG10116' differs from the female parent, the proprietary carnation plant '*Dianthus×allwoodii*' (unpatented), in that 'KLEDG10116' has white flowers with pink centers and medium growth, while '*Dianthus×allwoodii*' has light pink flowers and compact growth.

'KLEDG10116' differs from the male parent, the proprietary carnation plant 'Sinah' (unpatented), in that 'KLEDG10116' has white flowers with a pink center and small, green-blue leaves, while 'Sinah' has clear white flowers and wide, light green leaves.

We claim:

1. A new and distinct variety of carnation plant named 'KLEDG10116' as shown and described herein.

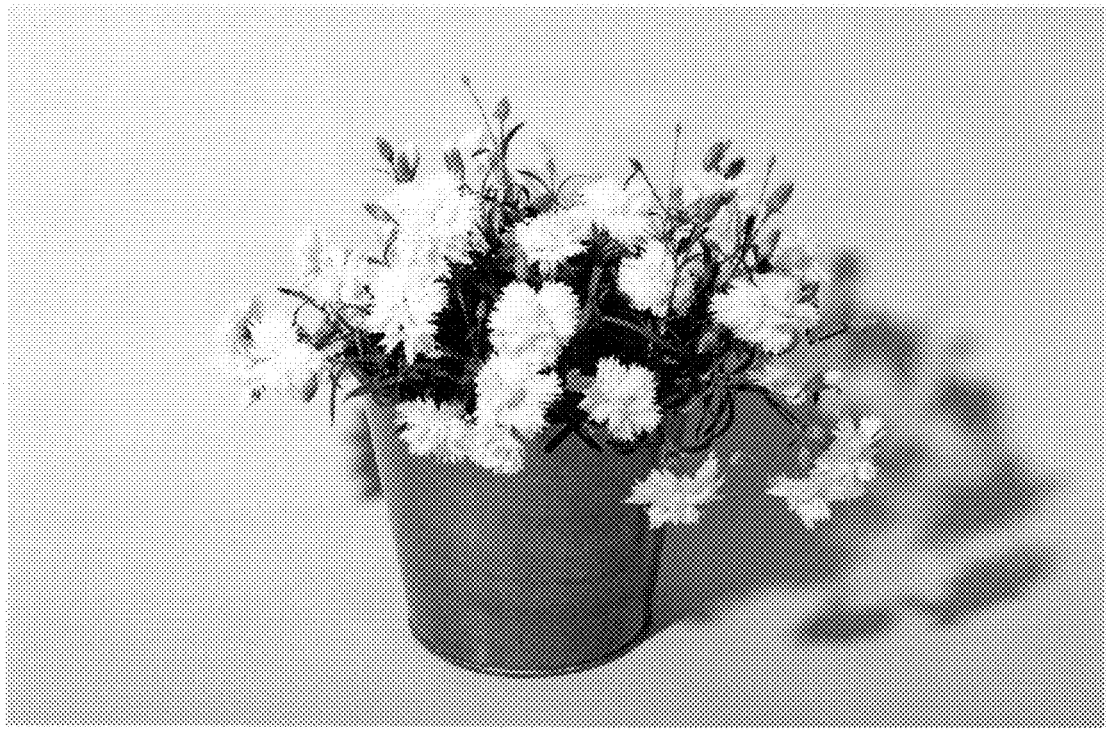

* * * * *